(12) United States Patent
Nierenberg et al.

(10) Patent No.: US 8,972,001 B2
(45) Date of Patent: *Mar. 3, 2015

(54) METHOD AND SYSTEM FOR DISPLAYING DATA (71) Applicant: Persyst Development Corporation, San Diego, CA (US)

(72) Inventors: Nicolas Nierenberg, La Jolla, CA (US); Scott B. Wilson, Del Mar, CA (US); Mark L. Scheuer, Wexford, PA (US)

(73) Assignee: Persyst Development Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,466

(22) Filed: Jan. 16, 2014

(65) Prior Publication Data
US 2014/0135643 A1 May 15, 2014

Related U.S. Application Data (63) Continuation-in-part of application No. 13/620,784, filed on Sep. 15, 2012, now Pat. No. 8,666,484.

(60) Provisional application No. 61/563,731, filed on Nov. 25, 2011.

(51) Int. Cl.
A61B 5/04 (2006.01)
A61B 5/00 (2006.01)
A61B 5/0478 (2006.01)
A61B 5/0476 (2006.01)

(52) U.S. Cl.
CPC ............. *A61B 5/742* (2013.01); *A61B 5/04012* (2013.01); *A61B 5/0478* (2013.01); *A61B 5/7207* (2013.01); *A61B 5/7203* (2013.01); *A61B 5/0476* (2013.01); *A61B 5/7225* (2013.01)
USPC .......................................... 600/544; 702/191

(58) Field of Classification Search
CPC ............. A61B 5/0476; A61B 5/04012; A61B 5/04017; A61B 5/7203; A61B 5/7207; A61B 5/72; A61B 5/742
USPC ........................... 600/544; 702/190, 191, 197
See application file for complete search history.

(56) References Cited

U.S. PATENT DOCUMENTS

2009/0264786 A1* 10/2009 Jacquin ........................ 600/544

* cited by examiner

*Primary Examiner* — Etsub Berhanu
(74) *Attorney, Agent, or Firm* — Clause Eight IPS; Michael Catania (57) ABSTRACT A method and system for displaying data is disclosed herein. A plurality of epochs are stitched together with an overlapping section in order to present a continuous EEG recording. Artifact reduction is performed on the epochs and then the epochs are combined together with overlapping sections of preferably two to four seconds.

8 Claims, 11 Drawing Sheets

METHOD AND SYSTEM FOR DISPLAYING DATA

CROSS REFERENCES TO RELATED APPLICATIONS

The Present Application is a continuation application of U.S. patent application Ser. No. 13/620,784, filed on Sep. 15, 2012, which claims priority to U.S. Provisional Patent Application No. 61/563,731, filed on Nov. 25, 2011, now abandoned, both of which are hereby incorporated by reference in their entireties.

STATEMENT REGARDING FEDERALLY SPONSORED RESEARCH OR DEVELOPMENT

Not Applicable

BACKGROUND OF THE INVENTION

1. Field of the Invention

The present invention generally relates to a method and system for displaying data. More specifically, the present invention relates to a method and system for displaying a continuous artifact reduced EEG report.

2. Description of the Related Art

An electroencephalogram ("EEG") is a diagnostic tool that measures and records the electrical activity of a person's brain in order to evaluate cerebral functions. Multiple electrodes are attached to a person's head and connected to a machine by wires. The machine amplifies the signals and records the electrical activity of a person's brain. The electrical activity is produced by the summation of neural activity across a plurality of neurons. These neurons generate small electric voltage fields. The aggregate of these electric voltage fields create an electrical reading which electrodes on the person's head are able to detect and record. An EEG is a superposition of multiple simpler signals. In a normal adult, the amplitude of an EEG signal typically ranges from 1 micro-Volt to 100 micro-Volts, and the EEG signal is approximately 10 to 20 milli-Volts when measured with subdural electrodes. The monitoring of the amplitude and temporal dynamics of the electrical signals provides information about the underlying neural activity and medical conditions of the person.

An EEG is performed to: diagnose epilepsy; verify problems with loss of consciousness or dementia; verify brain activity for a person in a coma; study sleep disorders, monitor brain activity during surgery, and additional physical problems.

Multiple electrodes (typically 17-21, however there are standard positions for at least 70) are attached to a person's head during an EEG. The electrodes are referenced by the position of the electrode in relation to a lobe or area of a person's brain. The references are as follows: F=frontal; Fp=frontopolar; T=temporal; C=central; P=parietal; O=occipital; and A=auricular (ear electrode). Numerals are used to further narrow the position and "z" points relate to electrode sites in the midline of a person's head. An electrocardiogram ("EKG") may also appear on an EEG display.

The EEG records brain waves from different amplifiers using various combinations of electrodes called montages. Montages are generally created to provide a clear picture of the spatial distribution of the EEG across the cortex. A montage is an electrical map obtained from a spatial array of recording electrodes and preferably refers to a particular combination of electrodes examined at a particular point in time.

In bipolar montages, consecutive pairs of electrodes are linked by connecting the electrode input 2 of one channel to input 1 of the subsequent channel, so that adjacent channels have one electrode in common. The bipolar chains of electrodes may be connected going from front to back (longitudinal) or from left to right (transverse). In a bipolar montage signals between two active electrode sites are compared resulting in the difference in activity recorded. Another type of montage is the referential montage or monopolar montage. In a referential montage, various electrodes are connected to input 1 of each amplifier and a reference electrode is connected to input 2 of each amplifier. In a reference montage, signals are collected at an active electrode site and compared to a common reference electrode.

Reference montages are good for determining the true amplitude and morphology of a waveform. For temporal electrodes, CZ is usually a good scalp reference.

Being able to locate the origin of electrical activity ("localization") is critical to being able to analyze the EEG. Localization of normal or abnormal brain waves in bipolar montages is usually accomplished by identifying "phase reversal," a deflection of the two channels within a chain pointing to opposite directions. In a referential montage, all channels may show deflections in the same direction. If the electrical activity at the active electrodes is positive when compared to the activity at the reference electrode, the deflection will be downward. Electrodes where the electrical activity is the same as at the reference electrode will not show any deflection. In general, the electrode with the largest upward deflection represents the maximum negative activity in a referential montage.

Some patterns indicate a tendency toward seizures in a person. A physician may refer to these waves as "epileptiform abnormalities" or "epilepsy waves." These include spikes, sharp waves, and spike-and-wave discharges. Spikes and sharp waves in a specific area of the brain, such as the left temporal lobe, indicate that partial seizures might possibly come from that area. Primary generalized epilepsy, on the other hand, is suggested by spike-and-wave discharges that are widely spread over both hemispheres of the brain, especially if they begin in both hemispheres at the same time.

There are several types of brain waves: alpha waves, beta waves, delta wave, theta waves and gamma waves. Alpha waves have a frequency of 8 to 12 Hertz ("Hz"). Alpha waves are normally found when a person is relaxed or in a waking state when a person's eyes are closed but the person is mentally alert. Alpha waves cease when a person's eyes are open or the person is concentrating. Beta waves have a frequency of 13 Hz to 30 Hz. Beta waves are normally found when a person is alert, thinking, agitated, or has taken high doses of certain medicines. Delta waves have a frequency of less than 3 Hz. Delta waves are normally found only when a person is asleep (non-REM or dreamless sleep) or the person is a young child. Theta waves have a frequency of 4 Hz to 7 Hz. Theta waves are normally found only when the person is asleep (dream or REM sleep) or the person is a young child. Gamma waves have a frequency of 30 Hz to 100 Hz. Gamma waves are normally found during higher mental activity and motor functions.

The following definitions are used herein.

"Amplitude" refers to the vertical distance measured from the trough to the maximal peak (negative or positive). It expresses information about the size of the neuron population and its activation synchrony during the component generation.

The term "analogue to digital conversion" refers to when an analogue signal is converted into a digital signal which can then be stored in a computer for further processing. Analogue signals are "real world" signals (e.g., physiological signals such as electroencephalogram, electrocardiogram or electrooculogram). In order for them to be stored and manipulated by a computer, these signals must be converted into a discrete digital form the computer can understand.

"Artifacts" are electrical signals detected along the scalp by an EEG, but that originate from non-cerebral origin. There are patient related artifacts (e.g., movement, sweating, ECG, eye movements) and technical artifacts (50/60 Hz artifact, cable movements, electrode paste-related).

The term "differential amplifier" refers to the key to electrophysiological equipment. It magnifies the difference between two inputs (one amplifier per pair of electrodes).

"Duration" is the time interval from the beginning of the voltage change to its return to the baseline. It is also a measurement of the synchronous activation of neurons involved in the component generation.

"Electrode" refers to a conductor used to establish electrical contact with a nonmetallic part of a circuit. EEG electrodes are small metal discs usually made of stainless steel, tin, gold or silver covered with a silver chloride coating. They are placed on the scalp in special positions.

"Electrode gel" acts as a malleable extension of the electrode, so that the movement of the electrodes leads is less likely to produce artifacts. The gel maximizes skin contact and allows for a low-resistance recording through the skin.

The term "electrode positioning" (10/20 system) refers to the standardized placement of scalp electrodes for a classical EEG recording. The essence of this system is the distance in percentages of the 10/20 range between Nasion-Inion and fixed points. These points are marked as the Frontal pole (Fp), Central (C), Parietal (P), occipital (O), and Temporal (T). The midline electrodes are marked with a subscript z, which stands for zero. The odd numbers are used as subscript for points over the left hemisphere, and even numbers over the right "Electroencephalogram" or "EEG" refers to the tracing of brain waves, by recording the electrical activity of the brain from the scalp, made by an electroencephalograph.

"Electroencephalograph" refers to an apparatus for detecting and recording brain waves (also called encephalograph).

"Epileptiform" refers to resembling that of epilepsy.

"Filtering" refers to a process that removes unwanted frequencies from a signal.

"Filters" are devices that alter the frequency composition of the signal.

"Montage" means the placement of the electrodes. The EEG can be monitored with either a bipolar montage or a referential one. Bipolar means that there are two electrodes per one channel, so there is a reference electrode for each channel. The referential montage means that there is a common reference electrode for all the channels.

"Morphology" refers to the shape of the waveform. The shape of a wave or an EEG pattern is determined by the frequencies that combine to make up the waveform and by their phase and voltage relationships. Wave patterns can be described as being: "Monomorphic". Distinct EEG activity appearing to be composed of one dominant activity. "Polymorphic". distinct EEG activity composed of multiple frequencies that combine to form a complex waveform. "Sinusoidal". Waves resembling sine waves. Monomorphic activity usually is sinusoidal. "Transient". An isolated wave or pattern that is distinctly different from background activity.

"Spike" refers to a transient with a pointed peak and a duration from 20 to under 70 msec.

The term "sharp wave" refers to a transient with a pointed peak and duration of 70-200 msec.

The term "neural network algorithms" refers to algorithms that identify sharp transients that have a high probability of being epileptiform abnormalities.

"Noise" refers to any unwanted signal that modifies the desired signal. It can have multiple sources.

"Periodicity" refers to the distribution of patterns or elements in time (e.g., the appearance of a particular EEG activity at more or less regular intervals). The activity may be generalized, focal or lateralized.

An EEG epoch is an amplitude of a EEG signal as a function of time and frequency.

Various techniques have been developed to present the EEG data to a physician or technician. However, these techniques are still lacking If the raw EEG report is presented to a physician or technician, then artifacts typically render the EEG report incapable of distinguishing brain activity such as a seizure from artifacts. Despite the use of artifact reduction algorithms, the failure to accurately distinguish true physiological rhythmicity from the artifacts is a serious shortcoming of current software systems and requires an expert assessment. What is needed is a way for a physician or technician to clearly compare the raw EEG report with a filtered report in order to better analyze the patient's brain activity. Visually inspecting a raw EEG and then reviewing a processed EEG is difficult since the y-axis and X-axis can be misplaced due to various processing techniques such as stitching. Further, channels may be overlapped adding to further difficulty in reading an EEG.

BRIEF SUMMARY OF THE INVENTION

The present invention provides an EEG system and method that overlays a processed EEG report over a raw EEG report to permit a physician or technician to clearly see the activity reported.

The present invention provides the ability to select short overlapping epochs where the results of artifact removal from each epoch is stitched together with the result from the next and previous epoch. This stitching can be accomplished many ways, but in a preferred method the signals from the two epochs are combined using a weighted average where the weight is proportional to the ratio of the distance to the epoch centers.

For example an epoch length of two seconds is selected with an increment (epoch step) of one second. Artifact removal using BSS and other techniques is performed on a set of channels for seconds one and two producing a two second length "clean" result. Then artifact removal is performed on seconds two and three producing an overlapping clean result. The results overlap in the second second of the record. For each channel, the weighted average of the two overlapping results produces a final result without discontinuities. In the portion of the second nearer the center of the first epoch the value from the first epoch is weighted higher, and likewise for the portion nearer the center of the second epoch. Those skilled in the pertinent art will recognize that different or variable epoch lengths or steps may be selected while moving through the record. Also a different stitching technique might be used.

One aspect of the present invention is a method for filtering artifacts from an EEG signal. The method includes generating an EEG signal from a machine comprising a plurality of electrodes, an amplifier and processor. The method also includes transforming the EEG signal from a set of channels into a plurality of epochs. Each of the plurality of epochs has an epoch duration length of less than or equal to two seconds and an increment of less than or equal to one second. The method also includes filtering artifacts from each of the plurality of epochs using a blind source separation algorithm to generate a plurality of clean epochs. The method also includes combining the plurality of clean epochs to generate a processed EEG recording.

Yet another aspect of the present invention is a method for filtering artifacts from an EEG signal using a blind source separation algorithm. The method includes generating an EEG signal from a machine comprising a plurality of electrodes, an amplifier and processor. The method also includes transforming the EEG signal from a set of channels into a plurality of epochs. The method also includes filtering artifacts from each of the plurality of epochs using a blind source separation algorithm to generate a plurality of clean epochs. The method also includes combining the plurality of clean epochs to generate a processed EEG recording.

Yet another aspect of the present invention is a system for filtering artifacts from an EEG signal. The system includes electrodes, an amplifier, a processor and a display. The electrodes generate EEG signals. The amplifier is connected to each of the electrodes by wires and amplifies the EEG signals. The processor is connected to the amplifier to generate an EEG recording from the EEG signals. The display is connected to the processor to display an EEG recording. The processor is configured to transform each of the plurality of EEG signals from a set of channels into a plurality of epochs, remove artifacts from each of the plurality of epochs using a blind source separation algorithm to generate a plurality of clean epochs, and combine the plurality of clean epochs to generate a processed EEG recording for display.

Yet another aspect of the present invention is a method for filtering artifacts from an EEG signal using a artifact removal algorithm. The method includes generating an EEG signal from a machine comprising a plurality of electrodes, an amplifier and processor. The method also includes transforming the EEG signal from a set of channels into a plurality of epochs. The method also includes filtering artifacts from each of the plurality of epochs using an artifact removal algorithm to generate a plurality of clean epochs. The method also includes combining the plurality of clean epochs to generate a processed EEG recording.

Yet another aspect of the present invention is a method for filtering artifacts from an EEG signal by selecting an epoch time and increment. The method includes generating an EEG signal for a patient from a machine comprising a plurality of electrodes attached to the patient, an amplifier and processor. The method also includes selecting an epoch time length and an epoch time increment. The method also includes filtering artifacts for each of a plurality of epochs using an artifact removal algorithm to generate a plurality of clean epochs. The method also includes assigning a weighted average to each of the plurality of clean epochs. The method also includes combining the plurality of clean epochs to overlap to generate a processed EEG recording without discontinuities.

Yet another aspect of the present invention is a system for filtering artifacts from an EEG signal. The system includes electrodes, a processor, and a display. The electrodes generate EEG signals. The processor is connected to the electrodes to generate an EEG recording from the EEG signals. The display is connected to the processor and displays an EEG recording. The processor is configured to select an epoch time length and an epoch time increment, filter artifacts for each of a plurality of epochs using an artifact removal algorithm to generate a plurality of clean epochs, assign a weighted average to each of the plurality of clean epochs, and combine the plurality of clean epochs to overlap to generate a processed EEG recording without discontinuities.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figures 1, 1A:
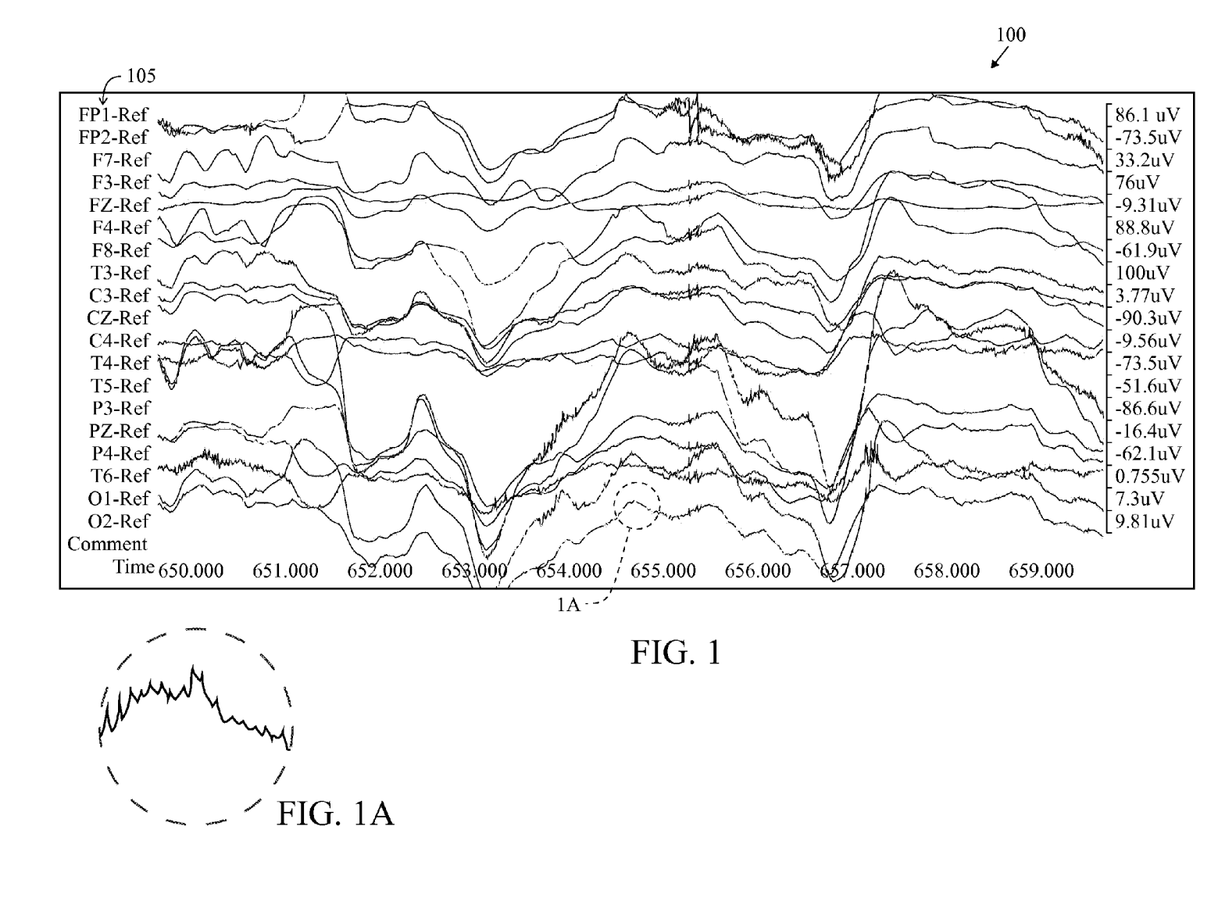
FIG. 1 is an illustration of a portion of a raw EEG report having nineteen channels.
FIG. 1A is an enlargement of circle 1A of FIG. 1.

A raw or original EEG report 100 is shown in FIG. 1. The original EEG report 100 has a plurality of channels FP1-Ref through to O2-Ref, shown at the Y axis 105 of the report. The X-axis of the report is time. The original EEG report 100 has not been subjected to artifact reduction. The original EEG report contains artifacts from various sources such as muscle movement, eye movement, sweating, electrode cables and the like. However, the EEG may also have certain activity that a physician or technician is looking for from the EEG report in order to accurately analyze the patient's brain activity. For example, the activity shown in FIG. 1A at a time 655.000 may represent a certain stage of brain activity for the patient that is important to the physician or technician. However, normally, the physician or technician will not review the raw EEG report 100 due to the presence of artifacts.

Figures 2, 2A:
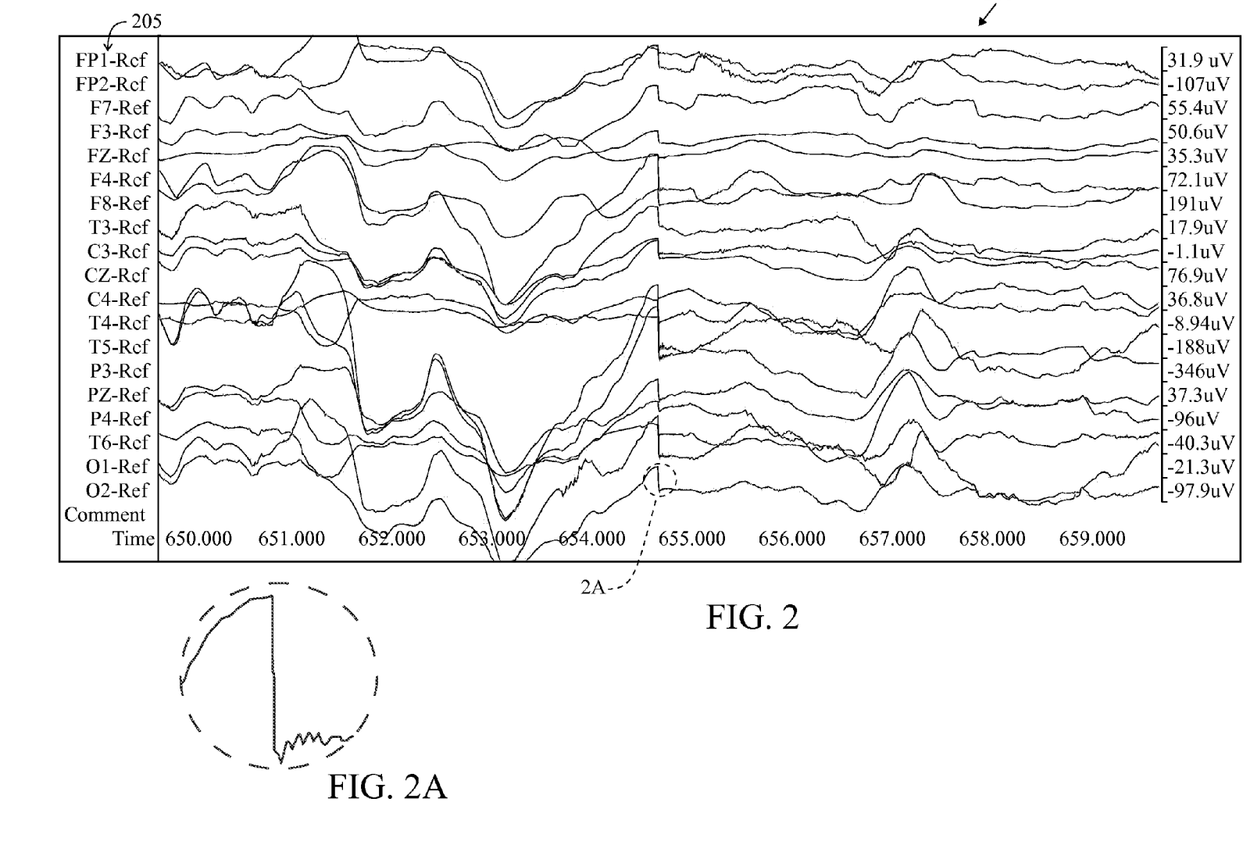
FIG. 2 is an illustration of a portion of a processed EEG report having nineteen channels in which epochs do not overlap.
FIG. 2A is an enlargement of circle 2A of FIG. 2.

FIG. 2 is an illustration of a processed EEG report 200 of the original EEG report 100 of FIG. 1 that has undergone artifact reduction and the stitching of epochs in order to recreate the EEG report, however, the epochs do not overlap resulting in lost information and/or discontinuities. The processed EEG report 200 has a plurality of channels FP1-Ref through to O2-Ref, shown at the Y axis 205 of the report. The X-axis of the report is time. As shown in FIG. 2A, the processed EEG report 200 at time 655.000 is quite different in appearance than the original EEG report 100 at time 655.000. This primarily due to stitching of epochs to recreate the EEG report, however if a physician or technician was only looking at the processed EEG report 200, the physician or technician would not be aware of the true activity at time 655.000.

Figures 3, 3A:
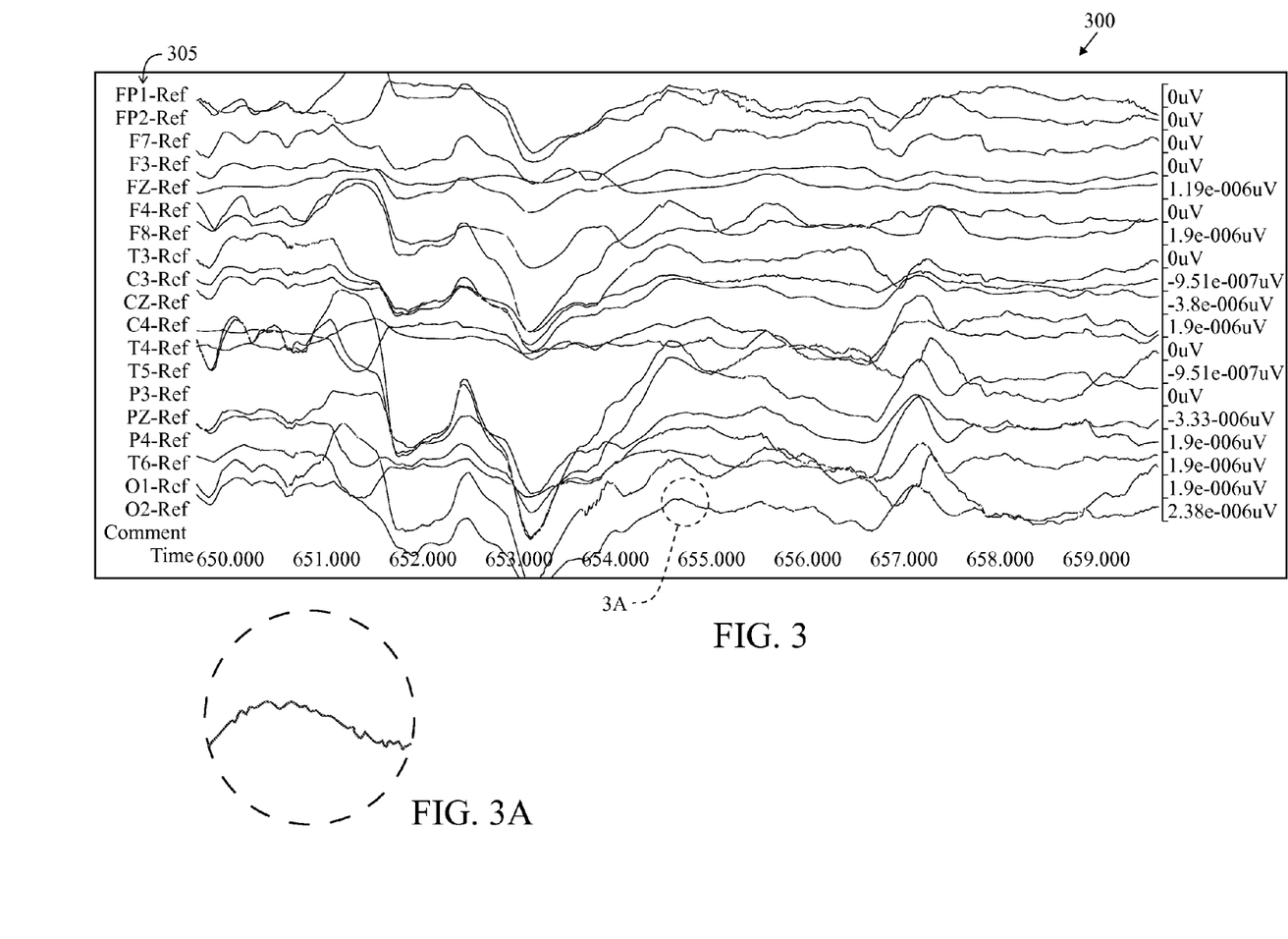
FIG. 3 is an illustration of a portion of a processed continuous EEG report in which sections of the epochs of the EEG report are stitched to overlap.
FIG. 3A is an enlargement of circle 3A of FIG. 3.

FIG. 3 is an illustration of a processed continuous EEG report 300 of the original EEG report 100 of FIG. 1 that has undergone artifact reduction and the stitching of overlapping epochs in order to recreate the EEG report. The processed EEG report 300 has a plurality of channels FP1-Ref through to O2-Ref, shown at the Y axis 305 of the report. The X-axis of the report is time. As shown in FIG. 3A, the processed EEG report 300 at time 655.000 is more similar in appearance to the original EEG report 100 at time 655.000 than the processed EEG report 200 of FIG. 2. However, there is still difficulty in analyzing a patient's brain activity by switching back and forth from an original EEG report 100 to a processed EEG report 200 or a processed continuous EEG report 300.

Figure 4:
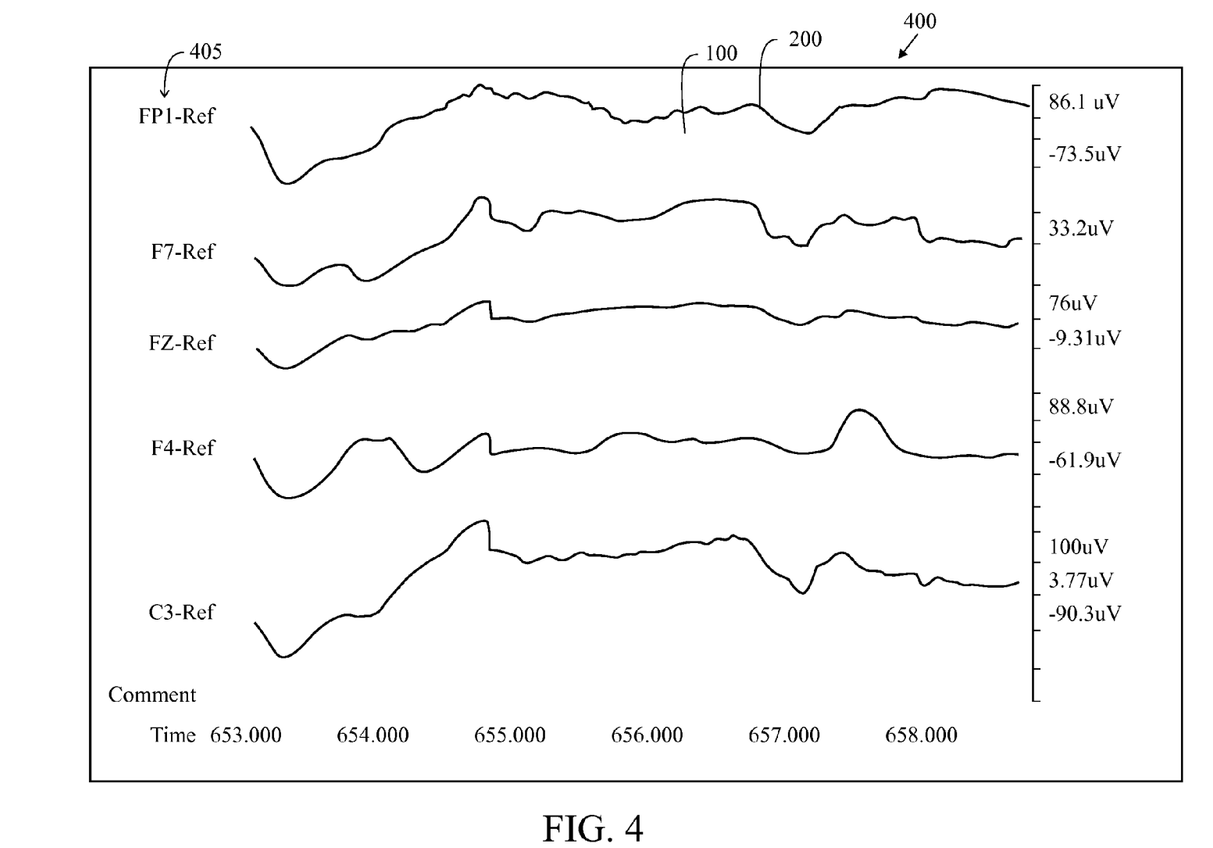
FIG. 4 is an illustration of a portion of processed continuous EEG report in which sections of the epochs of the EEG report are stitched to overlap.

FIG. 4 is an illustration of an EEG report 400, based on the EEG report 300 of FIG. 3, in which channels have been removed for a clearer illustration of channels. The illustration of the combined EEG report 400 only has five channels in order to clearly illustrate the invention, however, those skilled in the pertinent will recognize that the combined EEG report 400 could have sixteen, twenty, twenty-seven and any number of channels without departing from the scope and spirit of the present invention.

Figure 5:
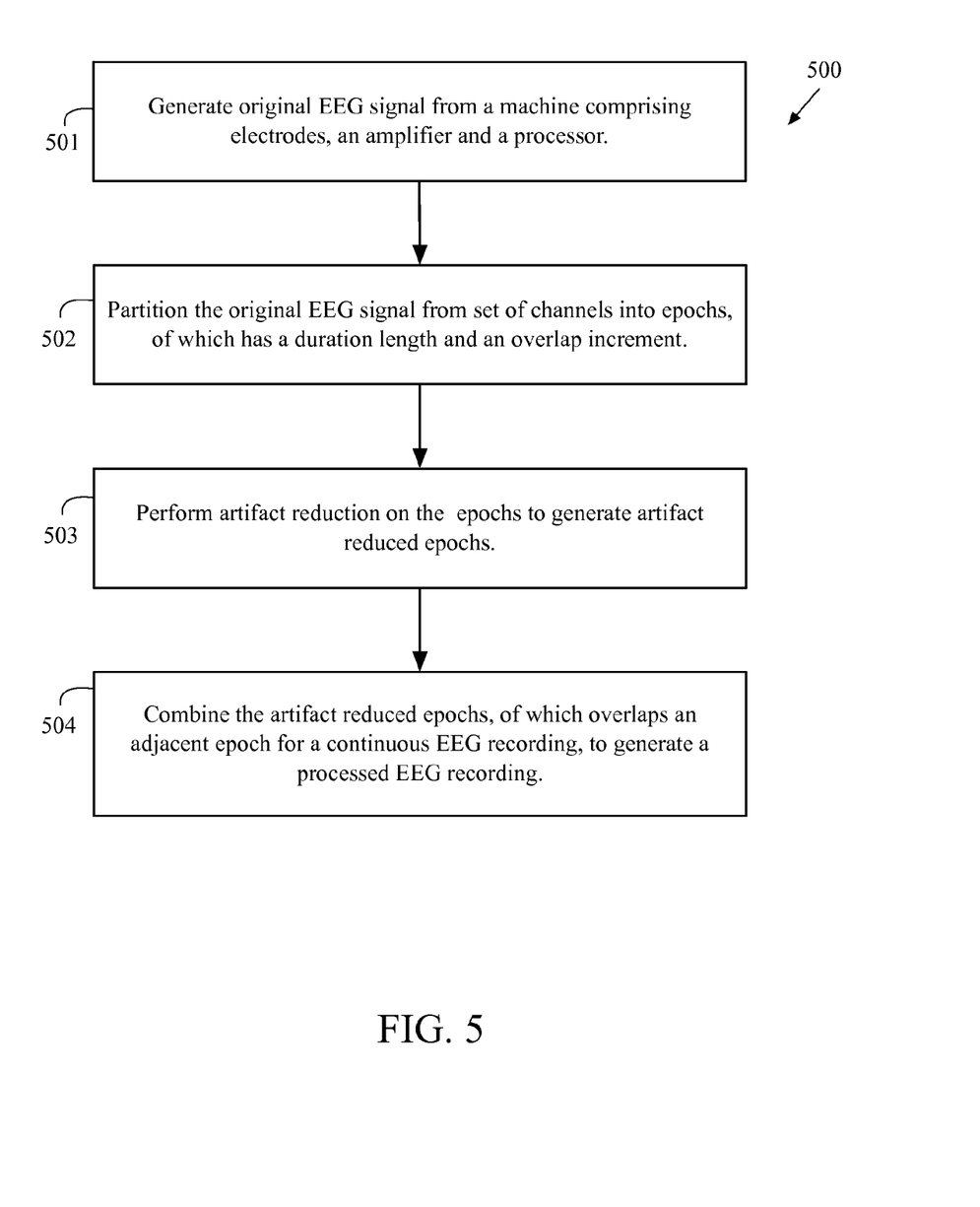
FIG. 5 is a flow chart of a method for displaying EEG data.
Figure 6:
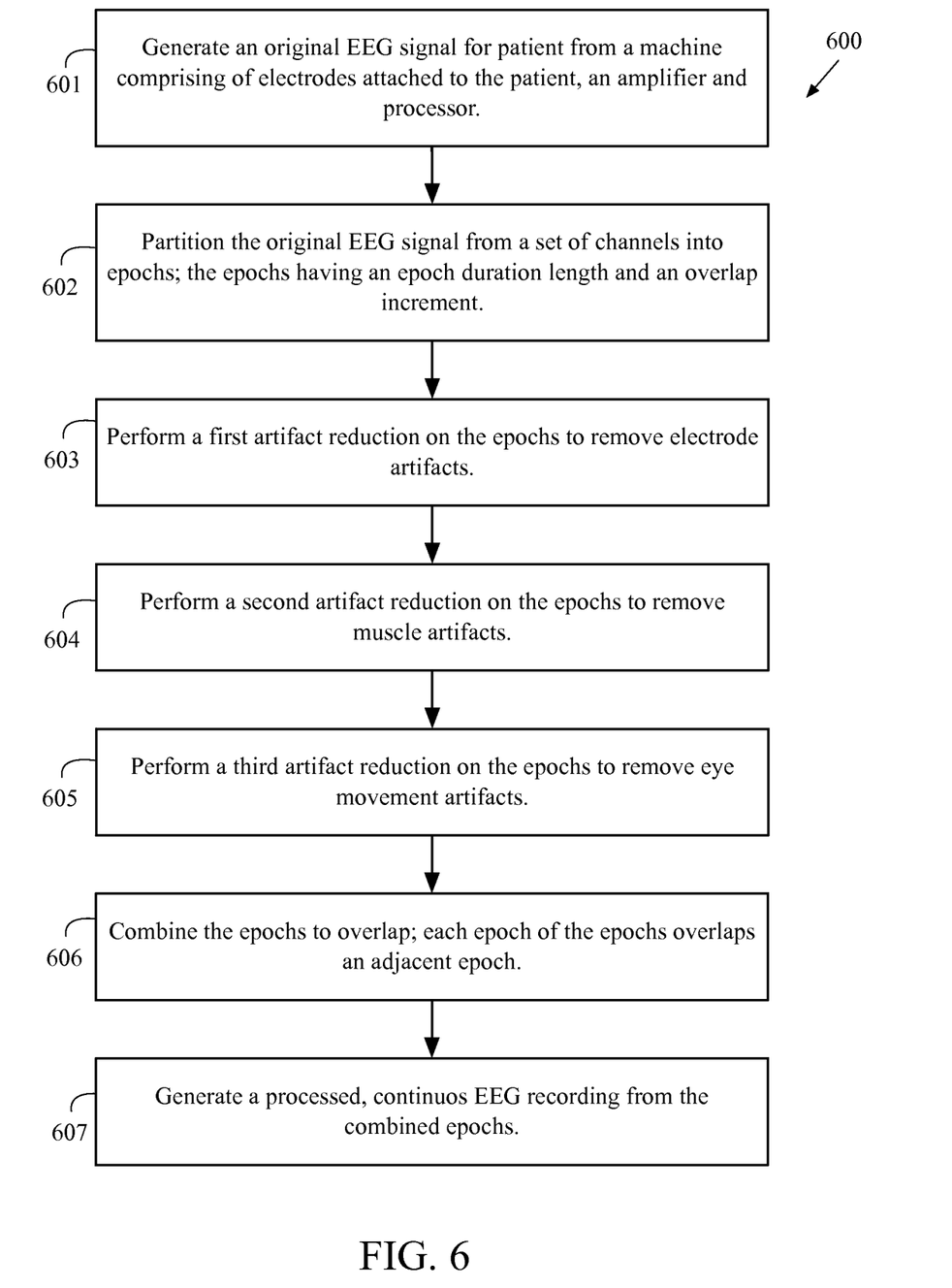
FIG. 6 is a flow chart for a method of artifact reduction.

A flow chart for a method 500 for displaying EEG data is shown in FIG. 5. At block 501, an original EEG report is generated from an EEG signal. The original EEG report is generated from an EEG machine comprising a plurality of electrodes and processor. The original EEG report comprises a first plurality of channels. At block 502, the original EEG signal is partitioned from a set of channels into epochs of which each has a predetermined duration length and an overlap increment. At block 503, artifact reduction is performed on the epochs to generate artifact reduced epochs. At block 504, the artifact reduced epochs are combined with overlapping adjacent epochs for a continuous EEG recording to generate a processed continuous EEG report. The stitched, overlapping epochs and continuous processed EEG report is displayed on a display screen, preferably a monitor. The stitched, overlapping epochs and continuous processed EEG report is not missing timeframes from stitching or creating discontinuities in the EEG report which is read by a physician or technician. All of the brain activity remains since the epochs overlap. The brain activity is preferably spikes, sharp waves, spike and wave discharges, artifacts, and the like FIG. 6 is a flow chart of a preferred method 600 for displaying EEG data. At block 601, an original EEG report is generated from an EEG signal for a patient from a machine preferably comprising electrodes attached to the patient, an amplifier and processor. At block 602, the original EEG signal is partitioned from a set of channels into a plurality of epochs. Each of the plurality of epochs having an epoch duration length and an overlap increment. At block 603, a first artifact reduction is performed on the plurality of epochs to remove electrode artifacts. At block 604, a second artifact reduction is performed on the plurality of epochs to remove muscle artifacts. At block 605, a third artifact reduction is performed on the plurality of epochs to remove eye movement artifacts. At block 606, the plurality of epochs are combined to overlap wherein each epoch of the plurality of epochs overlaps an adjacent epoch to form a processed continuous EEG report. At block 607, a processed continuous EEG recording is generated from the combined epochs.

Each of the plurality of epochs preferably has an epoch duration length of two seconds and an increment of one second. Alternatively, each of the plurality of epochs has an epoch duration length of four seconds and an increment of two seconds. The artifact removal algorithm is preferably a blind source separation algorithm. The blind source separation algorithm is preferably a CCA algorithm or an ICA algorithm. The clean epochs are preferably combined using a weighted average and the weight of the weighted average is preferably proportional to the ratio of the distance to an epoch center.

Figure 7:
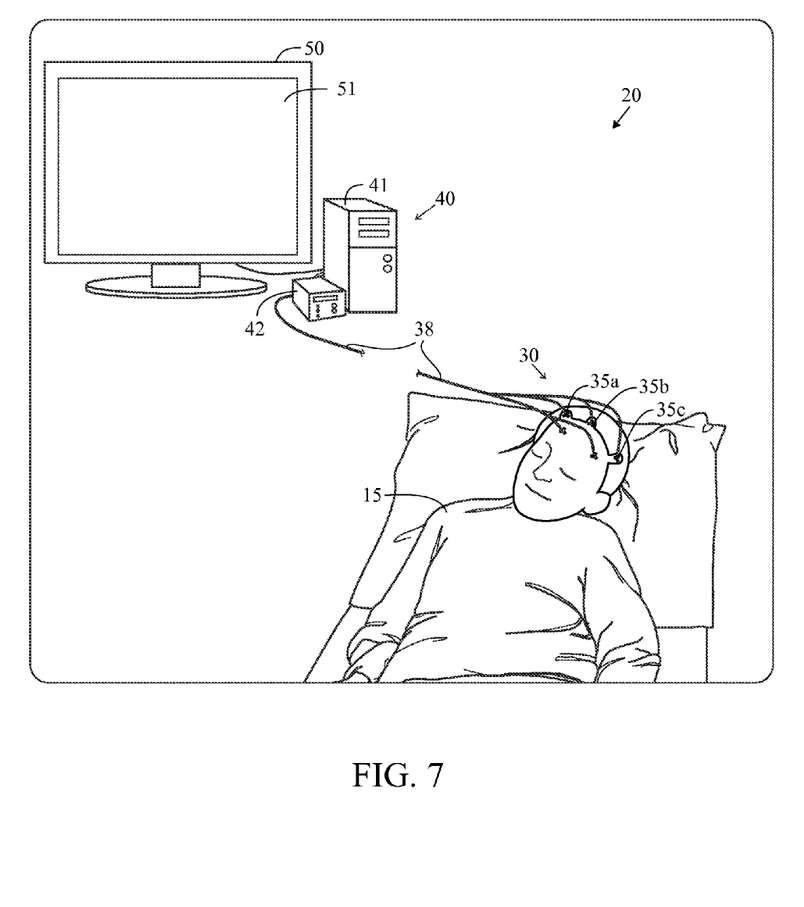
FIG. 7 is an illustration of an EEG system used on a patient.
Figure 10:
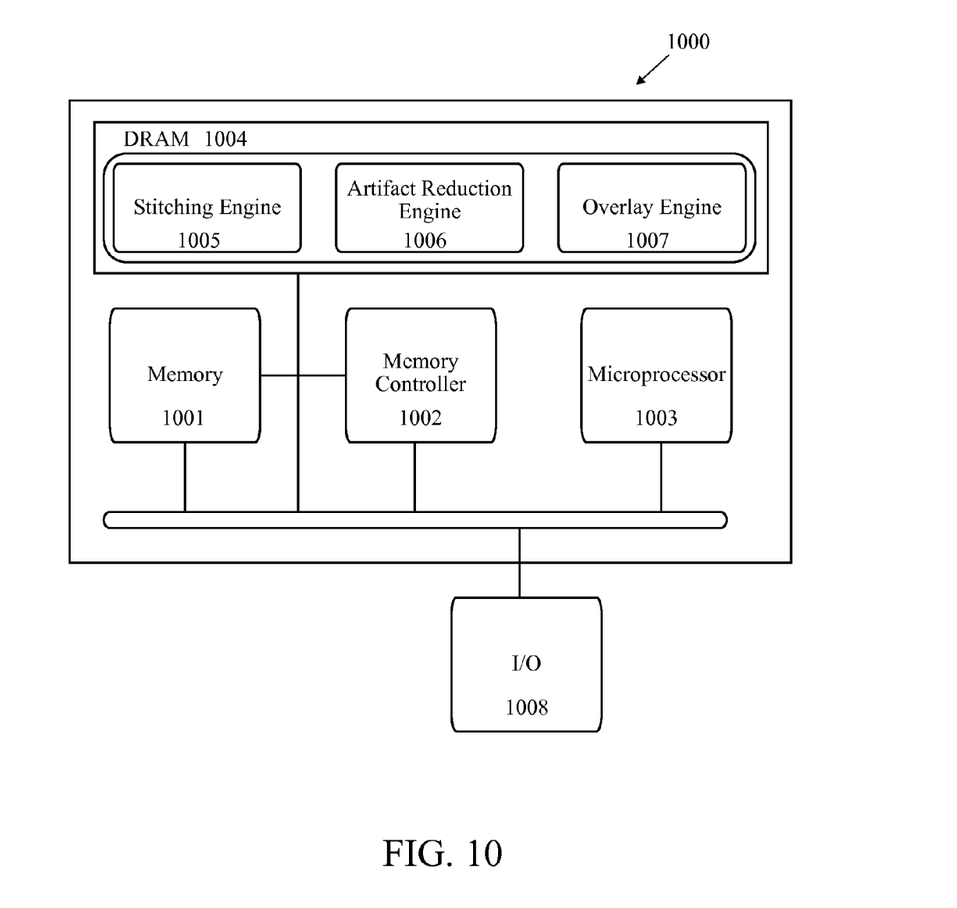
FIG. 10 is a block diagram of an EEG machine component of an EEG system.

As shown in FIG. 7, an EEG system is generally designated 20. The system preferably includes a patient component 30, an EEG machine component 40 and a display component 50. The patient component 30 includes a plurality of electrodes 35a, 35b, 35c attached to the patient 15 and wired by cables 38 to the EEG machine component 40. The EEG machine component 40 comprises a CPU 41 and an amplifier component 42. The EEG machine component 40 is connected to the display component 50 for display of the combined EEG reports, and for switching from a processed EEG report to the combined EEG reports, or from the processed EEG report to an original EEG report. As shown in FIG. 10, the EEG machine component 40 preferably includes a stitching engine 45, an artifact reduction engine 46, an overlay engine 47, a memory 41, a memory controller 42, a microprocessor 43, a DRAM 44, and an Input/Output 48. Those skilled in the pertinent art will recognize that the machine component 40 may include other components without departing from the scope and spirit of the present invention.

Figure 8:
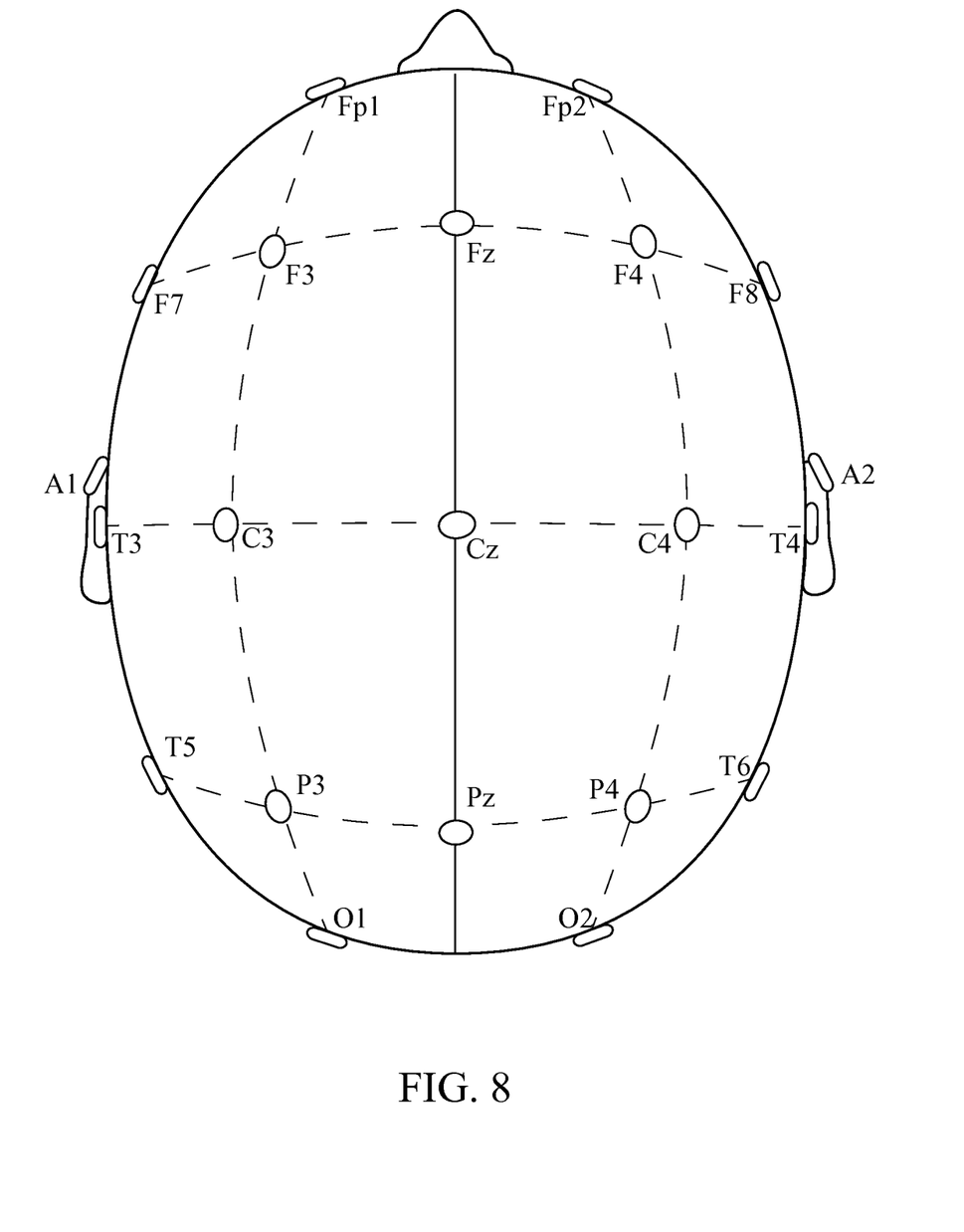
FIG. 8 is a map representing the international 10-20 electrode system for electrode placement for an EEG.
Figure 9:
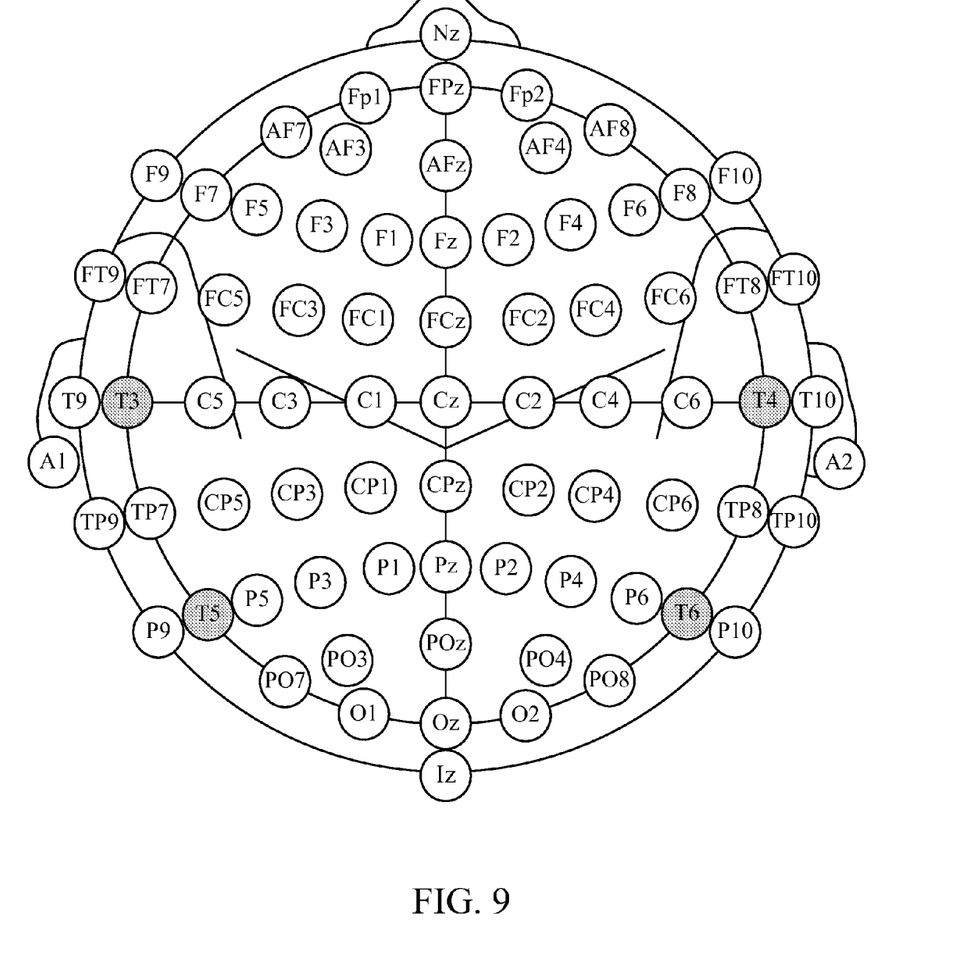
FIG. 9 is a detailed map representing the intermediate 10% electrode positions, as standardized by the American Electroencephalographic Society, for electrode placement for an EEG.

A patient has a plurality of electrodes attached to the patient's head with wires from the electrodes connected to an amplifier for amplifying the signal to a processor which is used to analyze the signals from the electrodes and create an EEG recording. The brain produces different signals at different points on a patient's head. Multiple electrodes are positioned on a patient's head as shown in FIGS. 8 and 9. For example Fp1 on FIG. 8 is represented in channel FP1-Ref on FIG. 4. The number of electrodes determines the number of channels for an EEG. A greater number of channels produces a more detailed representation of a patient's brain activity. Preferably, each amplifier of an EEG machine component 40 corresponds to two electrodes attached to a patient's head. The output from an EEG machine component is the difference in electrical activity detected by the two electrodes. The placement of each electrode is critical for an EEG report since the closer electrode pairs are to each other, the less difference in the brainwaves that are recorded by the EEG machine component. A more thorough description of an electrode utilized with the present invention is detailed in Wilson et al., U.S. Pat. No. 8,112,141 for a Method And Device For Quick Press On EEG Electrode, which is hereby incorporated by reference in its entirety. The EEG is optimized for automated artifact filtering. The EEG recordings are then processed using neural network algorithms to generate a processed EEG recording which is analyzed for display.

Algorithms for removing artifact from EEG typically use Blind Source Separation (BSS) algorithms like CCA (canonical correlation analysis) and ICA (Independent Component Analysis) to transform the signals from a set of channels into a set of component waves or "sources." The sources that are judged as containing artifact are removed and the rest of the sources are reassembled into the channel set.

Figure 11:
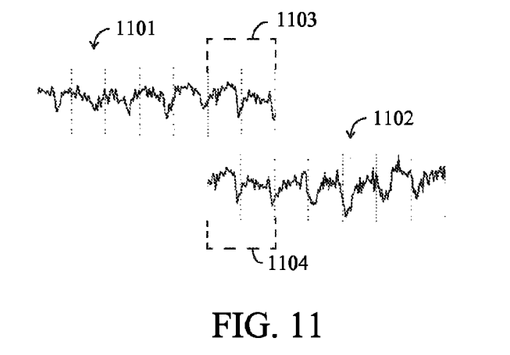
FIG. 11 is an illustration of isolated adjacent epochs.

FIG. 11 is an isolated view of adjacent unprocessed epochs 1101 and 1102. Epoch 1101 has an overlapping portion 1103 and epoch 1102 has an overlapping portion 1104. In this example, the overlapping portions 1103 and 1104 are approximately two seconds in length. Thus, overlapping portions 1103 and 1104 represent the same timeframe (two seconds) for raw EEG recording.

Figure 12:
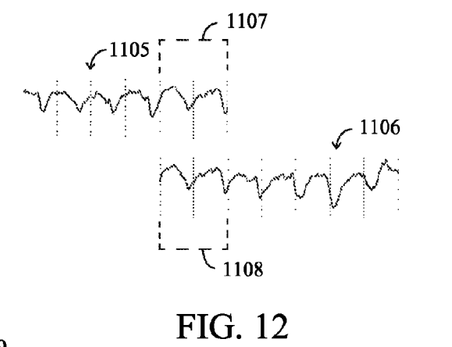
FIG. 12 is an illustration of isolated adjacent epochs.

FIG. 12 is an illustration of adjacent processed epochs 1105 and 1106. Artifact reduction has been performed on these epochs 1105 and 1106. Processed epochs 1105 and 1106 represent the same timeframe as unprocessed epochs 1101 and 1102. Thus, epoch 1105 is the result of artifact reduction of unprocessed epoch 1101, and epoch 1106 is the result of artifact reduction of unprocessed epoch 1102. Processed epoch 1105 has an overlapping portion 1107 and processed epoch 1106 has an overlapping portion 1108. Thus, overlapping portions 1107 and 1108 represent the same timeframe (two seconds) for the processed EEG recording. Further, overlapping portion 1107 is the same timeframe as overlapping portion 1103 and overlapping portion 1108 is the same timeframe as overlapping portion 1104. Further overlapping portions 1103, 1104, 1107 and 1108 represent all the same timeframe.

Figure 13:
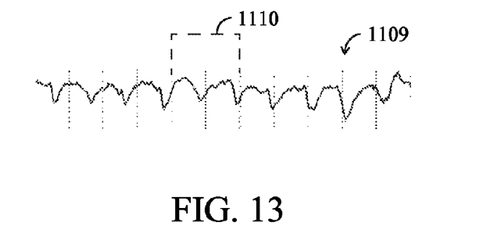
FIG. 13 is an illustration of epochs stitched together with an overlapping portion.

FIG. 13 is an illustration of the stitching of adjacent processed epochs 1105 and 1106 into a section of continuous processed EEG recording 1109. Portion 1110 is the overlapping portions 1107 and 1108 from adjacent processed epochs 1105 and 1106. As shown, no information is lost, and the processed EEG recording is continuous, without abrupt termination points where epochs have been stitched together.

Figure 14:
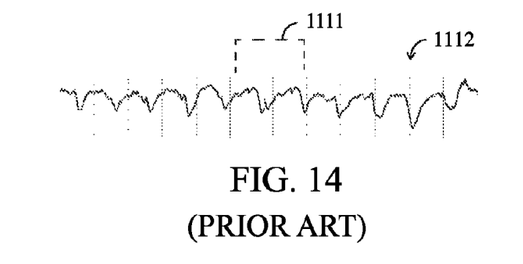
FIG. 14 is an example of prior art combining of epochs resulting in discontinuous or missing information from the processed and stitched EEG recording.

FIG. 14 is an illustration of the prior art approach of stitching of epochs without overlapping portions. The section 1112 of the processed EEG recording has a stitching portion 1111 which has changed from the same timeframe of the processed epochs 1105 and 1106. The stitching portion 1111 is different from section 1110 of FIG. 13.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention:

1. A method for generating a continuous EEG recording, the method comprising:
   generating an original EEG signal from a machine comprising a plurality of electrodes and a processor;
   partitioning the original EEG signal into a plurality of epochs, each of the plurality of epochs having an epoch duration length and an overlap increment;
   performing artifact reduction on the plurality of epochs to generate a plurality of artifact reduced epochs; and
   combining the plurality of artifact reduced epochs to generate a continuous processed EEG recording, wherein each of the plurality of artifact reduced epochs has an epoch duration length of two seconds and an increment of one second, wherein each of the plurality of artifact reduced epochs overlaps an adjacent artifact reduced epoch to produce the continuous processed EEG recording without discontinuities in the continuous processed EEG recording, wherein each of the plurality of artifact reduced epochs and the adjacent artifact reduced epoch are combined using a weighted average wherein the weight is proportional to a ratio of distances to epoch centers wherein a value from each of the plurality of artifact reduced epochs is weighted higher for an overlapping portion nearer a center of each of the plurality of artifact reduced epochs and a value from the adjacent artifact reduced epoch is weighted higher for an overlapping portion nearer a center of the adjacent artifact reduced epoch.

2. The method according to claim 1 wherein the artifact reduction is for at least one of muscle artifact, eye movement artifact, electrical artifact, heartbeat artifact, tongue movement artifact, and chewing artifact.

3. The method according to claim 1 further comprising illustrating the continuous processed EEG recording on a display, the display in communication with the processor wherein an operator switches from illustrating the continuous processed EEG recording to illustrating the original EEG signal.

4. A system for generating a continuous EEG recording, the system comprising:
   a plurality of electrodes for generating a plurality of EEG signals;
   a processor connected to the plurality of electrodes to generate an EEG recording from the plurality of EEG signals; and
   a display connected to the processor for displaying an original EEG signal and a processed EEG recording;
   wherein the processor is configured to partition the original EEG signal into a plurality of epochs, each of the plurality of epochs having an epoch duration length and an overlap increment, the processor is configured to perform artifact reduction on the plurality of epochs to generate a plurality of artifact reduced epochs, the processor is configured to combine the plurality of artifact reduced epochs to generate a continuous processed EEG recording, wherein each of the plurality of artifact reduced epochs overlaps an adjacent artifact reduced epoch to produce the continuous processed EEG recording without discontinuities in the continuous processed EEG recording, wherein the plurality of artifact reduced epochs are combined using a weighted average wherein each of the plurality of artifact reduced epochs and the adjacent artifact reduced epoch are combined using a weighted average wherein the weight is proportional to a ratio of distances to epoch centers wherein a value from each of the plurality of artifact reduced epochs is weighted higher for an overlapping portion nearer a center of each of the plurality of artifact reduced epochs and a value from the adjacent artifact reduced epoch is weighted higher for an overlapping portion nearer a center of the adjacent artifact reduced epoch.

5. The system according to claim 4 wherein the artifact reduction is for at least one of muscle artifact, eye movement artifact, electrical artifact, heartbeat artifact, tongue movement artifact, and chewing artifact.

6. The system according to claim 4 wherein each of the plurality of artifact reduced epochs has an epoch duration length of two seconds and an increment of one second.

7. The system according to claim 4 further comprising a display, the display in communication with the processor, wherein the display is configured to allow an operator to switch from illustrating the continuous processed EEG recording to illustrating the original EEG signal.

8. The system according to claim 4 wherein each of the plurality of artifact reduced epochs has an epoch duration length of four seconds and an increment of two seconds.

* * * * *